(12) United States Patent
Dams et al.

(10) Patent No.: US 7,495,118 B2
(45) Date of Patent: Feb. 24, 2009

(54) COMPOSITIONS CONTAINING C4-SWALLOW TAIL SILANES

(75) Inventors: Rudolf J. Dams, Antwerp (BE); Michael S. Terrazas, Prescott, WI (US); George G. I. Moore, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 530 days.

(21) Appl. No.: 11/027,404

(22) Filed: Dec. 30, 2004

(65) Prior Publication Data

US 2006/0147645 A1    Jul. 6, 2006

(51) Int. Cl.
    C07F 7/10    (2006.01)
(52) U.S. Cl. .......................... 556/413; 564/80; 564/95; 427/445
(58) Field of Classification Search ................ 516/413; 556/413
    See application file for complete search history.

(56) References Cited

U.S. PATENT DOCUMENTS

| | | | |
|---|---|---|---|
| 2,803,615 A | 8/1957 | Ahlbrecht et al. | |
| 3,423,234 A | 1/1969 | Heine | |
| 3,442,664 A | 5/1969 | Heine | |
| 3,492,394 A | 1/1970 | Heine | |
| 3,787,351 A | 1/1974 | Olson | |
| 3,906,027 A | 9/1975 | Muessdoerffer et al. | |
| 3,919,295 A | 11/1975 | Wechsberg et al. | |
| 4,167,639 A | 9/1979 | Billenstein et al. | |
| 5,207,996 A | 5/1993 | Sierakowski et al. | |
| 5,274,159 A | 12/1993 | Pellerite et al. | |
| 5,342,986 A | 8/1994 | Pohmer et al. | |
| 5,502,251 A | 3/1996 | Pohmer et al. | |
| 5,688,884 A | 11/1997 | Baker et al. | |
| 5,702,509 A | 12/1997 | Pellerite et al. | |
| 5,874,616 A | 2/1999 | Howells et al. | |
| 6,280,883 B1 | 8/2001 | Lamanna et al. | |
| 6,384,168 B1 | 5/2002 | Tanaka et al. | |
| 6,452,038 B1 | 9/2002 | Rao et al. | |
| 6,514,492 B1 | 2/2003 | Gao et al. | |
| 6,664,354 B2 | 12/2003 | Savu et al. | |
| 6,689,854 B2 | 2/2004 | Fan et al. | |
| 7,199,197 B2 | 4/2007 | Caldwell et al. | |
| 2005/0142563 A1 | 6/2005 | Haddad et al. | |
| 2006/0148671 A1* | 7/2006 | Dams et al. ................. | 510/494 |
| 2006/0149012 A1* | 7/2006 | Terrazas et al. ............ | 526/288 |
| 2007/0197401 A1* | 8/2007 | Arco et al. .................. | 507/233 |
| 2008/0008891 A1 | 1/2008 | Dams et al. | |

FOREIGN PATENT DOCUMENTS

| | | |
|---|---|---|
| EP | 1 225 187 | 7/2002 |
| EP | 1 225 188 | 7/2002 |
| EP | 1 329 548 | 7/2003 |
| EP | 1 369 453 | 12/2003 |
| GB | 2 218 097 | 11/1989 |
| JP | 60-126203 | 7/1985 |
| JP | 60126203 A * | 7/1985 |
| WO | WO 01/30873 | 5/2001 |
| WO | WO 02/16306 | 2/2002 |
| WO | WO 03/089712 | 10/2003 |
| WO | WO 2004/013225 | 2/2004 |

OTHER PUBLICATIONS

English translation of Yoshioka et al., JP 60-126203.*
E. Kissa, "Flourinated Surfactants", *Surfactants Science Series*, vol. 50, Marcel Dekker, NY (1994).

* cited by examiner

*Primary Examiner*—Mark Eashoo
*Assistant Examiner*—Peter F Godenschwager
(74) *Attorney, Agent, or Firm*—Kathleen B. Gross

(57) ABSTRACT

Described are perfluoro lower alkyl derived silanes having two perfluoroalkyl groups in close proximity to one another which in an organic solvent are useful in treating siliceous substrates; the compositions may optionally contain an additional non-fluorinated compound in a mixture or condensation product.

25 Claims, No Drawings

COMPOSITIONS CONTAINING C4-SWALLOW TAIL SILANES

FIELD OF THE INVENTION

The present invention relates to novel fluorochemical silanes containing two perfluoro-lower alkyl groups or "tails" in close proximity to one another, called "swallow tail" silanes. The novel silanes are useful as easy to clean treatments for silaceous substrates, for example, ceramics, ceramic tiles, glass, glass surfaces, and the like. The novel silanes are more effective in creating high oil and water repellent surfaces compared to single group or single tail silanes of the same lower molecular tail size.

BACKGROUND OF THE INVENTION

Fluorochemical compounds are well know and commercially used to coat or render various substrates oil- and water repellent and to provide other desirable properties thereto such as soil repellency and soil release.

Fluorochemical sulfonamido silanes having at least 4 carbon atoms in the fluoroalkyl group have been described for treating substrates in GB 2,218,097; U.S. Pat. Nos. 5,274,159; 5,702,509; and earlier in 3,492,394; 3,423,234; and 3,442,664.

In addition, fluorochemical oligomeric silanes having at least 4 carbon atoms in the fluoroalkyl group have been described for treating hard surfaces, such as glass or ceramics in EP 1,369,453; EP 1,225,187, and EP 1,225,188.

Despite the many known fluorochemical compositions to provide repellency properties to a substrate, there continues to be a desire to find further compositions that may have improved initial repellency properties and/or that have improved durability, i.e., the repellency properties last longer even under abrading conditions.

Accordingly, it is desirable to provide a coating composition capable of providing a highly durable water, oil and/or stain repellent coating on a substrate. In particular, it is desirable to provide a durable coating wherein the initial, repellent properties are substantially maintained, even under abrading conditions. Further, the coating compositions preferably can be applied and used in an environmental friendly way and can be produced in a reliable, convenient and cost effective way. Additionally, the coatings desirably have a good durability against exposure to UV light, i.e. the repellency properties do not substantially degrade upon exposure to UV light. Furthermore, it is desirable to obtain optically clear coatings in particular when transparent substrates such as glass are to be treated with the compositions.

SUMMARY OF THE INVENTION

In one aspect, the present invention provides a fluorochemical composition containing one or more silanes of the formula I:

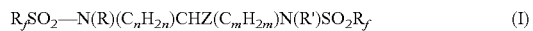

wherein $R_f$ is each independently $C_pF_{2p+1}$, where p is 2 to 5;

R is a $C_1$ to $C_4$ alkyl or an aryl group;

m and n are both integers greater than 0;

Z is H or a group of the formula: $(C_{m'}H_{2m'})X-Q-Si(Y)_3$, in which m' is 0 to 4, X is O, S or NH and Q is —C(O)NH—(CH$_2$)$_{n'}$— or —(CH$_2$)$_{n'}$—, and R is as defined above; and R' is R or, when Z is H, a group of the formula —(CH$_2$)$_{n'}$—Si(Y)$_3$; n' is an integer of 1 to 20, and Y is a hydrolysable group.

In a second aspect, the present invention includes a fluorochemical composition as above described with an organic solvent in an amount sufficient to dissolve and/or disperse the silane(s).

A third aspect of the present invention provides the above described fluorochemical composition and one or more compounds of the formula II:

wherein

M is selected from Si, Ti, Zr, Al, V, Sn, and Zn;

R" is a non-hydrolyzable group;

Y is a hydrolysable group such as OR, OCOCH$_3$ or Cl;

q is 0, 1 or 2, and r is 4, 3 or 2.

A fourth aspect of the present invention provides the combination of one or more silanes of formula I and one or more compounds of formula II with an organic solvent in an amount sufficient to dissolve and/or disperse both components.

The present invention also includes methods of treating silaceous substrates by applying to at least a portion of the surface of the substrate a fluorochemical composition containing one or more silanes of formula I and, optionally one or more compounds of formula II in an organic solvent.

The compositions of the present invention are efficient and effective oil and water repellents for siliceous surfaces, such as sanitary ceramics, ceramic tiles and glass. They provide superior overall performance to that of the single tail perfluoro C4 silanes and comparable performance to perfluoro C8 silanes. The compositions are substantially free of fluorochemical compounds that eliminate slowly from living organisms and are therefore considered environmentally sustainable vis a vis materials which are based on building blocks containing a longer perfluorinated group (tail).

Many previously known fluorochemical materials contain perfluorooctyl moieties. These surfactants ultimately degrade to perfluorooctyl-containing compounds. It has been reported that certain perfluorooctyl-containing compounds may tend to bio-accumulate in living organisms; this tendency has been cited as a potential concern regarding some fluorochemical compounds. For example, see U.S. Pat. No. 5,688,884 (Baker et al.). As a result, there is a desire for fluorine-containing compositions which are effective in providing desired surfactant properties, and which eliminate more effectively from the body (including the tendency of the composition and its degradation products).

It is expected that the fluorochemical materials of the present invention, which contain perfluorobutyl moieties, when exposed to biologic, thermal, oxidative, hydrolytic, and photolytic conditions found in the environment, will break down to various degradation products. For example, compositions comprising perfluorobutylsulfonamido moieties are expected to degrade, at least to some extent, ultimately to perfluorobutylsulfonate salts. It has been surprisingly found that perfluorobutylsulfonate, tested in the form of its potassium salt, eliminates from the body much more effectively than perfluorohexylsulfonate and even more effectively than perfluorooctylsulfonate.

DETAILED DESCRIPTION OF THE INVENTION

The fluorochemical composition contains one or more silanes of the formula I $$R_fSO_2-N(R)(C_nH_{2n})CHZ(C_mH_{2m})N(R')SO_2R_f \quad (I)$$

wherein $R_f$ is each independently $C_pF_{2p+1}$, where p is 2 to 5;

R is a $C_1$ to $C_4$ alkyl or an aryl group;

m and n are both integers greater than 0;

Z is H or a group of the formula: $(C_mH_{2m})X-Q-Si(Y)_3$, in which m' is 0 to 4, X is O, S or NH and Q is —C(O)NH—$(CH_2)_{n'}$— or —$(CH_2)_{n'}$, and R is as defined above; and R' is R or, when Z is H, a group of the formula —$(CH_2)_{n'}$—Si$(Y)_3$; n' is an integer of 1 to 20, and Y is a hydrolysable group.

The perfluoroalkylsulfonamido groups ($R_fSO_2N$—) may be the same or different. The perfluoroalkyl may each contain 2-5 carbon atoms, but preferably each has 4 carbon atoms.

In the above silanes of formula I, one embodiment has m as an integer from 1 to 6 and n as an integer from 1 to 6.

The term "alkyl" is defined as having 1-4 carbon atoms and includes, for example, methyl or ethyl.

The term "aryl" means an aromatic group such as phenyl which is unsubstituted or may be substituted by one or up to five substituents such as alkyl, as above defined, alkoxy of 1 to 4 carbon atoms, halo, e.g. fluoro, chloro, bromo, iodo, hydroxy, amino, nitro and the like. Halo and alkyl substituents are preferred.

In the above silanes, one embodiment has R defined as independently —$CH_3$ or —$CH_2CH_3$.

In the above silanes of formula I, n' may also vary from 1-10 and in one embodiment may be 3.

A hydrolysable group, Y, in the silanes of formula I may be the same as defined for Y in the compounds of formula II below.

Representative fluorochemical compounds of the invention include, but are not limited to, $[C_4F_9SO_2N(CH_3)CH_2]_2$ CHOCH$_2$CH$_2$CH$_2$Si(OCH$_3$)$_3$, $[C_4F_9SO_2N(CH_3)CH_2]_2$ CHOCONHCH$_2$CH$_2$CH$_2$Si(OCH$_3$)$_3$, and $C_4F_9SO_2N(CH_3)$CH$_2$CH$_2$CH$_2$N(SO$_2$C$_4$F$_9$)CH$_2$CH$_2$CH$_2$Si(OCH$_3$)$_3$.

The fluorochemical compounds of the invention may be prepared by known methods. For example, $[C_4F_9SO_2N(CH_3)CH_2]_2$CHOH may be made by reacting two moles of $C_4F_9SO_2NH(CH_3)$ with either 1,3-dichloro-2-propanol or epichlorohydrin in the presence of base. $[C_4F_9SO_2N(CH_3)CH_2]_2$CHOCH$_2$CH$_2$CH$_2$Si(OCH$_3$)$_3$ can be made from $[C_4F_9SO_2N(CH_3)CH_2]_2$CHOH by alkylation with ClCH$_2$CH$_2$CH$_2$Si(OCH$_3$)$_3$ or by alkylation with allyl chloride, followed by hydrosilation with HSiCl$_3$ and methanolysis. Reaction of $[C_4F_9SO_2N(CH_3)CH_2]_2$CHOH with OCNCH$_2$CH$_2$CH$_2$Si(OCH$_3$)$_3$ yields $[C_4F_9SO_2N(CH_3)CH_2]_2$ CHOCONHCH$_2$CH$_2$CH$_2$Si(OCH$_3$)$_3$.

The composition of the present invention may include one or more organic solvents. The organic solvent or blend of organic solvents used must be capable of dissolving one or more silanes of formula I and, optionally a mixture of the silanes with one or more compounds of formula II, described below.

Suitable organic solvents, or mixtures of solvents include aliphatic alcohols, such as methanol, ethanol, isopropanol; ketones such as acetone or methyl ethyl ketone; esters such as ethyl acetate, methylformate, and ethers such as diethyl ether or dipropyleneglycol monomethylether (DPM).

In the fluorochemical composition of the present invention, one or more silanes of formula I may be combined with one or more compounds of formula II $$M(R'')_q(Y)_{r-q} \quad (II)$$

wherein M is selected from Si, Ti, Zr, Al, V, Sn, and Zn;

R" is a non-hydrolyzable group;

Y is a hydrolysable group;

q is 0, 1 or 2, and r is 4, 3 or 2.

In the combination of silanes of formula I and compounds of formula II, the combination may be a mixture or a condensation product obtainable after a substantially complete condensation reaction of said one or more fluorochemical silanes and said one or more non-fluorinated compounds of formula II. By the term "substantially complete condensation reaction" is meant that the reaction is either complete or at least 80% of the hydrolysable groups in the mixture have disappeared, preferably at least 90%. Completion of the reaction can be monitored through the use of infrared spectroscopy and $C^{13}$-NMR.

In a further aspect, the present invention provides a composition comprising a condensation product obtainable after a partial condensation reaction of said one or more fluorochemical oligomers and said one or more non-fluorinated compounds. By "partial condensation" and "partial condensate" in connection with the present invention is meant that some of the hydrolysable groups in the mixture have reacted while leaving a substantial amount of hydrolysable groups available for a condensation reaction. Typically, a partial condensate means that at least 20%, preferably at least 30%, more preferably at least 50% of the hydrolysable groups are still available for further condensation reaction.

The term "hydrolysable group" in connection with the present invention refers to a group which either is directly capable of undergoing condensation reactions under appropriate conditions or which is capable of hydrolyzing under appropriate conditions, thereby yielding a compound, which is capable of undergoing condensation reactions. Appropriate conditions include acidic or basic aqueous conditions, optionally in the presence of another condensation catalyst, such as Sn-compounds.

The hydrolysable groups Y may be the same or different and are generally capable of hydrolyzing under appropriate conditions, for example under acidic or basic aqueous conditions, such that the fluorochemical oligomer can participate in condensation reactions. Preferably, the hydrolysable groups upon hydrolysis yield groups capable of undergoing condensation reactions, such as silanol groups.

Examples of hydrolysable groups include halogens such as chlorine, bromine, iodine or fluorine, alkoxy groups —OR' (wherein R' represents a lower alkyl group, preferably containing 1 to 6, more preferably 1 to 4 carbon atoms and which may optionally be substituted by one or more halogen atoms), acyloxy groups —O(CO)—R" (wherein R" represents a lower alkyl group, preferably containing 1 to 6, more preferably 1 to 4 carbon atoms and which may optionally be substituted by one or more halogen atoms), aryloxy groups —OR''' (wherein R''' represents an aryl moiety, preferably containing 6 to 12, more preferably containing 6 to 10 carbon atoms, which may be optionally substituted by one or more substituents independently selected from halogens, and $C_1$ to $C_4$ alkyl groups which may optionally be substituted by one or more halogen atoms). In the above formulae R', R", and R''' may include linear, branched and/or cyclic structures. Specific examples of hydrolysable groups include methoxy, ethoxy and propoxy group, chlorine.

The non-hydrolyzable groups R" may be the same or different and are generally not capable of hydrolyzing under conditions for condensation reactions, e.g., acidic or basic aqueous conditions where hydrolysable groups are hydrolyzed. The non-hydrolyzable groups R" may be independently a hydrocarbon group, for example an alkyl group, preferably from 1-4 carbon atoms as defined above for R or an aryl group also as defined above for R.

Representative examples of compounds of formula (II) include tetramethoxysilane, tetraethoxysilane (TEOS), methyltriethoxysilane (MTEOS), dimethyldiethoxysilane (DDS), tetraethylhexyltitanate and the like.

The combination or condensation product of silanes of formula I and compounds of formula II may also contain organic solvents as defined above in an amount sufficient to dissolve the compounds.

The weight ratio of compounds (I) to (II) are from about 100:0 to 1:99; a preferred ratio is between 50:50 and 10:90.

Where the combination of silanes of formula I and compounds of formula II is a condensation product, the reaction product is obtainable by reacting the components and an optional crosslinking agent. Typically, the reaction product is a partial condensate or alternatively a substantial complete condensation product is formed.

The polycondensation reaction is conveniently carried out by mixing the starting components in an organic solvent preferably at room temperature, in the presence of sufficient water to effect hydrolysis of the hydrolysable groups. Preferably, the amount of water will be between 0.1 and 20% by weight of the total composition, more preferably between 1 and 10% by weight. In addition to water, an organic or inorganic acid or base catalyst should preferably be used.

Organic acid catalysts include acetic acid, citric acid, formic acid, triflic acid, perfluorobutyric acid and the like. Examples of inorganic acids include sulphuric acid, hydrochloric acid and the like. Examples of useful base catalysts include sodium hydroxide, potassium hydroxide, sodium fluoride, potassium fluoride and triethylamine. The acid or base catalyst will generally be used in amounts between about 0.01 and 10%, more preferably between 0.05 and 5% by weight of the total composition.

The composition of the present invention, comprising the compounds of formula I and II and optional crosslinking agent, and/or the partial or complete polycondensation products thereof, is generally applied to the substrate in amounts sufficient to produce a coating that is water and oil repellent. This coating can be extremely thin, e.g., 1 to 50 molecular layers, though in practice a useful coating may be thicker.

Suitable substrates that can be treated in a particularly effective way with the fluorochemical composition, comprising the fluorochemical condensate mixture, of this invention include substrates having a hard surface that preferably has groups capable of reacting with the fluorinated condensate. Particularly preferred substrates include ceramics and glass. Various articles can be effectively treated with the fluorochemical composition of the present invention to provide a water and oil repellent coating thereon. Examples include ceramic tiles, bathtubs or toilets, glass shower panels, construction glass, various parts of a vehicle (such as the mirror or windscreen), glass, and ceramic or enamel pottery materials.

Treatment of the substrates results in rendering the treated surfaces less retentive of soil and more readily cleanable due to the oil and water repellent nature of the treated surfaces. These desirable properties are maintained despite extended exposure or use and repeated cleanings because of the high degree of durability of the treated surface as can be obtained through the compositions of this invention.

To effect the treatment of a substrate, the fluorochemical composition, preferably in the form of a solvent composition as disclosed above, is applied to the substrate. The amount of fluorochemical composition to be coated on the substrate will generally be that amount sufficient to produce a coating which is water and oil repellent, such a coating having at 20° C. a contact angle with distilled water of at least 80° C., and a contact angle with n-hexadecane of at least 40° C., measured after drying and curing of the coating.

Preferably, the substrate should be clean prior to applying the compositions of the invention so as to obtain optimum characteristics, particularly durability. That is, the surface of the substrate to be coated should be substantially free of organic contamination prior to coating. Cleaning techniques depend on the type of substrate and include, for example, a solvent washing step with an organic solvent, such as acetone or ethanol.

In accordance with a preferred embodiment, compositions for application to a substrate are prepared by diluting a concentrate comprising a solution of at least 25% by weight of solids in an organic solvent, by adding to the concentrate an organic solvent or mixture of solvents.

A wide variety of coating methods can be used to apply a composition of the present invention, such as brushing, spraying, dipping, rolling, spreading, and the like. A preferred coating method for application of the fluorochemical composition includes spray application. A substrate to be coated can typically be contacted with the treating composition at room temperature (typically, about 20° C. to about 25° C.). Alternatively, the mixture can be applied to substrates that are preheated at a temperature of for example between 60° C. and 150° C. This is of particular interest for industrial production, where e.g. ceramic tiles can be treated immediately after the baking oven at the end of the production line. Following application, the treated substrate can be dried and cured at ambient or elevated temperature, e.g., at 40° C. to 300° C. and for a time sufficient to dry and cure. Alternatively, in addition with a thermal treatment, the coating composition may be cured by irradiation (e.g. by means of UV-irradiators, a laser, etc.) in a manner known per se, depending on the type and presence, respectively of an initiator. The process may also require a polishing step to remove excess material.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Milwaukee, Wis., or may be synthesized by conventional methods.

Preparation of $[C_4F_9SO_2N(CH_3)CH_2]_2CHOH$

A three necked round bottom 1000 mL flask, fitted with a stirrer, heating mantle, condenser, nitrogen inlet, Dean-Stark trap and thermometer was charged with $C_4F_9SO_2N(CH_3)H$ (313.0 g; 1 mole), as prepared in U.S. Pat. No. 6,664,354, Example 1, Part A, which patent is incorporated herein by reference, dimethylformamide (100.0 g) and heptane (40.0 g). The mixture was heated to reflux and dried by azeotropic distillation. The mixture was cooled to about 30° C. under nitrogen purge, and NaOCH3 (30% in methanol; 180.0 g 1 mole) was added. The mixture was heated at 50° C. for one hour, stripping off methanol under vacuum from an aspirator.

1,3-dichloro-2-propanol (65.0 g; 0.5 mole) was added to the flask and the temperature was elevated to 80° C. and held overnight. The ensuing mixture was washed with DI water (300 mL at 80° C.) three times and the remaining organic layer was separated and dried in an oven at 120° C. for 1 hour. Analysis of the resulting yellow brown solid was consistent with [$C_4F_9SO_2N(CH_3)CH_2$]$_2$CHOH.

Preparation of FC-1; [$C_4F_9SO_2N(CH_3)CH_2$]$_2$CHOC(O)NH($CH_2$)$_3$Si(OCH$_2$CH$_3$)$_3$ A three necked round bottom 500 mL flask fitted with a stirrer, heating mantle, condenser, nitrogen inlet, Dean-Stark trap and thermometer was charged with [$C_4F_9SO_2N(CH_3)CH_2$]$_2$CHOH (204.6 g; 0.3 mole), and methylethyl ketone (250.0 g; available from Sigma-Aldrich, Milwaukee, Wis.). The mixture was heated and approximately 50 g of material was removed using the Dean-Stark trap. The mixture was cooled to 30° C. and OCN(CH$_2$)$_3$Si(OCH$_2$CH$_3$)$_3$ (74.4 g) and three drops of stannous actuate were added. The mixture was heated to 75° C. under nitrogen for 16 hours. A clear, slightly yellow product ensued. Analysis of the product was consistent with [$C_4F_9SO_2N(CH_3)CH_2$]$_2$CHOC(O)NH(CH$_2$)$_3$Si(OCH$_2$CH$_3$)$_3$.

Preparation of FC-2; [$C_4F_9SO_2N(CH_3)CH_2$]$_2$CHO(CH$_2$)$_3$Si(OCH$_2$CH$_3$)$_3$ A three necked round bottom 500 mL flask fitted with a stirrer, heating mantle, condenser, nitrogen inlet, Dean-Stark trap and thermometer was charged with [$C_4F_9SO_2N(CH_3)CH_2$]$_2$CHOH (204.6 g; 0.3 mole), dimethylformamide (100.0 g; available from Sigma-Aldrich, Milwaukee, Wis.) and heptane (40.0 g). The mixture was heated at 100° C. under aspiration vacuum, and the heptane was removed using the Dean-Stark trap. NaOCH3 (54.0 g; 0.3 mole; 30% in methanol) was added and the ensuing mixture was heated at 50° C. for 1 hour under nitrogen. Methanol was stripped using a rotary evaporator and ClCH$_2$CH$_2$CH$_2$Si(OCH$_3$)$_3$ (59.4 g) was added. The mixture was heated to 75° C. under nitrogen overnight. The ensuing mixture was filtered, and stripped of solvent using a rotary evaporator. The mixture was further distilled at 180-200° C. (at 0.1 mm Hg (13.3 Pa)) yielding a yellow viscous liquid. Analysis of the liquid was consistent with the structure [$C_4F_9SO_2N(CH_3)CH_2$]$_2$CHO(CH$_2$)$_3$Si(OCH$_3$)$_3$.

Preparation of Test Solutions

Test solutions for Examples 1-7 and Comparative Example C-1 were prepared by combining 1.0 g. of the compositions listed in Table 1 together with 37% HCl (1.0 g) and ethanol (98.0 g).

Coating of Test Solutions

The Test Solutions were sprayed onto pre-cleaned, white sanitary ceramic tiles (available from Sphinx, Maastricht, Netherlands) at room temperature, at a rate of about 40 mL/minute.

Contact Angle Measurement

The treated substrates were tested for their static contact angles versus water and n-hexadecane using an Olympus TGHM goniometer (Olympus Corp, Pompano Beach Fla.). The static contact angles were measured before ("initial"), immediately after abrasion ("after abrasion"), and after being exposed for 16 hours to 18% HCl ("after HCl treatment") unless otherwise indicated. The values reported are the mean values of 4 measurements and are reported in degrees (Table 2).

TABLE 1

Compositions of Examples 1-7 and Comparative Example C-1.

| Example No. | FC-1 (g) | FC-2 (g) | TEOS (g) | MTEOS (g) | DDS (g) | FC-3* (g) |
|---|---|---|---|---|---|---|
| 1 | 1.0 | — | — | — | — | — |
| 2 | — | 1.0 | — | — | — | — |
| 3 | 0.5 | — | 0.5 | — | — | — |
| 4 | 0.10 | — | 0.9 | — | — | — |
| 5 | 0.10 | — | 0.45 | 0.45 | — | — |
| 6 | 0.10 | — | 0.45 | — | 0.45 | — |
| 7 | — | 0.10 | 0.90 | — | — | — |
| C-1 | — | — | — | — | — | 1.0 |

— indicates none added

FC-3 is $C_8F_{17}SO_2N(CH_2CH_3)CH_2CH_2CH_2Si(OCH_2CH_3)_3$

TABLE 2

Contact Angles in degrees for water/hexadecane for Examples 1-7 and Comparative Example C-1.

| | Contact Angle Water/Hexadecane (°) | | |
|---|---|---|---|
| Example No. | Initial | After Abrasion | After HCl treatment |
| 1 | 108/68 | 78/53 | 99/62 |
| 2 | 98/66 | 72/52 | 95/60 |
| 3 | 105/64 | 76/53 | 95/64 |
| 4 | 110/67 | 80/52 | 95/60 |
| 5 | 108/63 | 82/50 | 98/60 |
| 6 | 112/61 | 75/50 | 95/55 |
| 7 | 105/64 | 78/54 | 92/59 |
| C-1 | 105/64 | 78/46 | 95/58 |

The above specification, examples and data provide a complete description of the manufacture and use of the composition of the invention. Since many embodiments of the invention can be made without departing from the spirit and scope of the invention, the invention resides in the claims hereinafter appended.

We claim:

1. A fluorochemical composition comprising: one or more silanes of the formula:

$$R_f SO_2—N(R)(C_n H_{2n})CHZ(C_m H_{2m})N(R')SO_2 R_f \qquad (I)$$

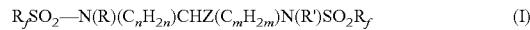

wherein $R_f$ is each independently $C_p F_{2p+1}$, where p is 2 to 5;

R is a $C_1$ to $C_4$ alkyl or an aryl group;

m and n are both integers greater than 0;

Z is H or a group of the formula: $(C_{m'}H_{2m'})$X-Q-Si(Y)$_3$, in which m' is 0 to 4, X is O, S or NH and Q is —C(O)NH—(CH$_2$)$_{n'}$— or —(CH$_2$)$_{n'}$—, and R is as defined above; and R' is R or, when Z is H, a group of the formula —(CH$_2$)$_{n'}$—Si(Y)$_3$; n' is an integer of 1 to 20, and Y is a hydrolysable group.

2. A composition according to claim 1, where p is 4; m is 1 to 6, and n is 1 to 6.

3. A composition according to claim 2, wherein Z is —O-Q-Si(Y)$_3$, in which Y is independently —Cl, or a $C_1$-$C_4$ alkoxy group.

4. A composition according to claim 3, wherein Q is —(CH$_2$)$_{n'}$—, where n' is 1 to 10.

5. A composition according to claim 3, wherein Q is —C(O)NH(CH$_2$)$_{n'}$— where n' is 1 to 10.

6. A composition according to claim 2, wherein Z is hydrogen and R' is —$(CH_2)_{n'}$—Si(Y), in which Y is independently —Cl, or a $C_1$ to $C_4$ alkoxy group.

7. A composition according to claim 2, wherein R is —$CH_3$ or —$CH_2CH_3$.

8. A composition according to claim 2, wherein the sum of n and m is 2; X is O, and Q is —$C(O)NH(CH_2)_3$—.

9. A composition according to claim 1, comprising one or more silanes of the formulae $[C_4F_9SO_2N(CH_3)CH_2]_2CHOCH_2CH_2CH_2Si(OCH_3)_3$,
$[C_4F_9SO_2N(CH_3)CH_2]_2CHOCONHCH_2CH_2CH_2Si(OCH_3)_3$, and
$C_4F_9SO_2N(CH_3)CH_2CH2CH_2N(SO_2C_4F_9)CH_2CH_2CH_2Si(OCH_3)_3$.

10. A composition according to claim 1, further comprising an organic solvent.

11. A composition according to claim 10, wherein the solvent is an alcohol, ether, ketone or ester, or a mixture thereof.

12. A composition according to claim 1, further comprising one or more compounds of the formula:

$$M(R'')_q(Y)_{r-q} \quad (II)$$

wherein M is selected from Si, Ti, Zr, Al, V, Sn, and Zn;
R" is a non-hydrolyzable group;
Y is a hydrolysable group;
q is 0, 1 or 2, and
r is 4, 3 or 2.

13. A composition according to claim 12, wherein R" is R.

14. A composition according to claim 12, wherein Y is independently —Cl, or a $C_1$-$C_4$ alkoxy group.

15. A composition according to claim 12, wherein M is Si; R" is —$CH_3$ or —$CH_2CH_3$; and Y is independently —Cl, —$OCH_3$ or —$OCH_2CH_3$.

16. A composition according to claim 12, wherein the compound of formula II is tetramethoxysilane, tetraethoxysilane, methyltriethoxysilane, dimethyldiethoxysilane, or tetraethylhexyltitanate.

17. A composition according to claim 12, wherein the weight ratio of compounds I to II are from about 100:0 to about 1:99.

18. A composition according to claim 12, wherein the weight ratio of compounds I to II are from about 50:50 to about 10:90.

19. A composition according to claim 1, wherein Z is a group of the formula:

$$(C_mH_{2m'})X-Q-Si(Y)_3.$$

20. A fluorochemical composition comprising:
(a) one or more silanes of the formula:

$$R_fSO_2-N(R)(C_nH_{2n})CHZ(C_mH_{2m})N(R')SO_2R_f \quad (I)$$

wherein $R_f$ is each independently $C_pF_{2p+1}$, where p is 2 to 5;
R is a $C_1$ to $C_4$ alkyl or an aryl group;
m and n are both integers greater than 0;
Z is H or a group of the formula: $(C_mH_{2m'})X-Q-Si(Y)_3$, in which m' is 0 to 4, X is O, S or NH and Q is —C(O)NH—$(CH_2)_{n'}$— or —$(CH_2)_{n'}$—, and R is as defined above; and
R' is R or, when Z is H, a group of the formula —$(CH_2)_{n'}$—$Si(Y)_3$; n' is an integer of 1 to 20, and Y is a hydrolysable group;

(b) one or more compounds of the formula:

$$M(R'')_q(Y)_{r-q} \quad (II)$$

wherein M is selected from Si, Ti, Zr, Al, V, Sn, and Zn;
R" is R;
Y is independently —Cl, or -a $C_1$ to $C_4$ alkoxy group;
q is 0, 1 or 2, and
r is 4, 3 or 2; and (c) an organic solvent.

21. A composition according to claim 20 wherein p is 4.

22. A composition according to claim 20 comprising a condensation product of one or more silanes of the formula I and one or more compounds of the formula II.

23. A composition according to claim 20, wherein Z is a group of the formula:

$$(C_mH_{2m'})X-Q-Si(Y)_3.$$

24. A method of treating a siliceous substrate comprising applying to said substrate a composition according to claim 10.

25. A method of treating a siliceous substrate comprising applying to said substrate a composition according to claim 20.

* * * * *

UNITED STATES PATENT AND TRADEMARK OFFICE
CERTIFICATE OF CORRECTION

| | | |
|---|---|---|
| PATENT NO. | : 7,495,118 B2 | |
| APPLICATION NO. | : 11/027404 | |
| DATED | : February 24, 2009 | |
| INVENTOR(S) | : Rudolf J. Dams | |

It is certified that error appears in the above-identified patent and that said Letters Patent is hereby corrected as shown below:

Title Page, Column 2 (Foreign Patent Documents
Line 6, above "JP 60126203 A  *  7/1985" delete "JP   60-126203   7/1985".
(Repeated entry).

Title Page, Column 2 (Other Publications)
Line 2, delete "Flourinated" and insert in place thereof -- Fluorinated --.

Column 2
Line 19, delete "or2" and insert in place thereof -- or 2 --.

Column 3
Line 12, delete "$(C_mH_{2m})X-Q-Si(Y)_3$," and insert in place thereof
-- $(C_{m'}H_{2m'})X-Q-Si(Y)_3$, --.

Line 40, delete "$[C_4F_9SO_2N(CH)_3)CH_2]_2$" and insert in place thereof
-- $[C_4F_9SO_2N(CH_3)CH_2]_2$ --.

Line 41, delete "$[C_4F_9SO_2N(CH)_3)CH_2]_2$" and insert in place thereof
-- $[C_4F_9SO_2N(CH_3)CH_2]_2$ --.

Line 42, delete "$C_4F_9SO_2N(CH)_3)$" and insert in place thereof
-- $C_4F_9SO_2N(CH_3)$ --.

Line 46, delete "$(CH)_3)CH_2]_2CHOH$" and insert in place thereof
-- $(CH_3)CH_2]_2CHOH$ --.

Line 47, delete "$C_4F_9SO_2NH(CH)_3)$" and insert in place thereof
-- $C_4F_9SO_2NH(CH_3)$ --.

Signed and Sealed this
Fifteenth Day of February, 2011

David J. Kappos
*Director of the United States Patent and Trademark Office*

CERTIFICATE OF CORRECTION (continued)
U.S. Pat. No. 7,495,118 B2

Column 5
Line 44, delete "formula" and insert in place thereof -- formulae --.

Column 6
Line 65, delete "NaOCH3" and insert in place thereof -- NaOCH$_3$ --.

Column 7
Line 35, delete "NaOCH3" and insert in place thereof -- NaOCH$_3$ --.

Column 8
Line 16, before "indicate" insert -- – --.

Line 67, in Claim 5, delete "—C(O)NH(CH$_2$)$_n$—" and insert in place thereof -- —C(O)NH(CH$_2$)$_n$— --.

Column 9
Line 13, in Claim 9, delete "C$_4$F$_9$SO$_2$N(CH$_3$)CH$_2$CH2CH$_2$N(SO$_2$C$_4$F$_9$)" and insert in place thereof -- C$_4$F$_9$SO$_2$N(CH$_3$)CH$_2$CH$_2$CH$_2$N(SO$_2$C$_4$F$_9$) --.

Column 10
Line 25, in Claim 20, before "a" delete "-".